United States Patent
Liu

(10) Patent No.: US 7,632,962 B2
(45) Date of Patent: Dec. 15, 2009

(54) HYDROGENATION PROCESS AND CATALYSTS

(75) Inventor: Zhufang Liu, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/787,496

(22) Filed: Apr. 17, 2007

(65) Prior Publication Data

US 2007/0255070 A1  Nov. 1, 2007

Related U.S. Application Data

(60) Provisional application No. 60/795,124, filed on Apr. 26, 2006.

(51) Int. Cl.
C07C 69/74 (2006.01)
(52) U.S. Cl. .................................................. 560/127
(58) Field of Classification Search ................ 560/127; 556/186; 568/343
See application file for complete search history.

(56) References Cited

U.S. PATENT DOCUMENTS

| | | | |
|---|---|---|---|
| 3,334,149 A | 8/1967 | Akin et al. | |
| 3,622,645 A * | 11/1971 | Carr et al. ................. | 585/265 |
| 4,212,824 A | 7/1980 | Seagraves | |
| 5,286,898 A | 2/1994 | Gustafson et al. | |
| 5,319,129 A | 6/1994 | Gustafson et al. | |
| 5,399,742 A * | 3/1995 | Tennant et al. ............ | 560/127 |
| 6,180,559 B1 | 1/2001 | Roberts et al. | |
| 6,284,917 B1 * | 9/2001 | Brunner et al. ............ | 560/127 |
| 6,545,115 B2 | 4/2003 | Breunig et al. | |
| 6,670,301 B2 | 12/2003 | Adzic et al. | |
| 6,797,667 B2 | 9/2004 | Ruth et al. | |
| 6,861,387 B2 | 3/2005 | Ruth et al. | |
| 2003/0054950 A1 | 3/2003 | Zoeller et al. | |
| 2003/0086862 A1 | 5/2003 | Tsou et al. | |
| 2004/0158112 A1 | 8/2004 | Ramani et al. | |
| 2004/0226863 A1 | 11/2004 | Uzio et al. | |
| 2005/0101481 A1 | 5/2005 | Ruth et al. | |
| 2005/0159292 A1 | 7/2005 | Pham et al. | |
| 2006/0088741 A1 | 4/2006 | Yan et al. | |
| 2006/0135359 A1 | 6/2006 | Adzic et al. | |

FOREIGN PATENT DOCUMENTS

| | | |
|---|---|---|
| EP | 0069514 | 1/1983 |
| JP | 4004135642 | 5/1992 |
| JP | 405058734 | 3/1993 |
| JP | 2000073195 | 3/2000 |
| JP | 2001096157 | 4/2001 |
| JP | 2005059006 | 3/2005 |
| WO | 94/29261 | 12/1994 |

OTHER PUBLICATIONS

Principles of Catalyst Development, James T. Richardson, 1989, pp. 28-35.
Brunauer, S., Emmet, P.H., and Teller, E., J. Am. Chem. Soc., 60, 309-16 (1938).

* cited by examiner

*Primary Examiner*—Porfirio Nazario Gonzalez
(74) *Attorney, Agent, or Firm*—Louis N. Moreno; Bernard J. Graves, Jr.

(57) ABSTRACT

Disclosed is a process for the preparation of dimethyl cyclohexanedicarboxylates by the hydrogenation of the corresponding dimethyl benzenedicarboxylate ester in the presence of supported catalysts comprising (i) a Group VIII metal and (ii) a catalyst support material selected from graphite and silicon carbide.

16 Claims, No Drawings

HYDROGENATION PROCESS AND CATALYSTS

CROSS REFERENCE TO RELATED APPLICATIONS

This application claims the benefit of U.S. Provisional Application No. 60/795,124, filed Apr. 26, 2006

FIELD OF THE INVENTION

This invention pertains to processes for the preparation of dimethyl cyclohexanedicarboxylates by the hydrogenation of the corresponding dimethyl benzenedicarboxylate esters. More specifically, the present invention pertains to processes for the hydrogenation of a dimethyl benzenedicarboxylate ester in the presence of certain, novel, supported catalysts comprising (i) a Group VIII metal and (ii) a catalyst support material selected from graphite and silicon carbide.

BACKGROUND OF THE INVENTION

Dimethyl cyclohexanedicarboxylates (DMCD) are valuable chemicals used in the manufacture of coating resins as well as in the production of cyclohexanedimethanol (CHDM), an important monomer for the preparation of condensation polymers. One method of production of DMCD and CHDM comprises hydrogenation of dimethyl terephthalate (DMT) in the presence of a heterogeneous catalyst comprising palladium supported on a catalyst support material such as dehydrated or activated alumina, kieselguhr, activated carbon, dehydrated zirconium dioxide, dehydrated silica gel, chromium oxide, bentonite, and asbestos. Another method producing DMCD from DMT uses catalysts consist of palladium with a second Group VIII metal such as nickel and an alumina support in which the crystalline phase of the alumina is alpha, theta, delta, gamma, or a mixture thereof.

BRIEF SUMMARY OF THE INVENTION

In one embodiment the present invention provides processes for the preparation of dimethyl cyclohexanedicarboxylates by the catalytic hydrogenation of dimethyl benzenedicarboxylates in the presence of hydrogen and a catalyst comprising a Group VIII metal deposited on a catalyst support material selected from graphite and silicon carbide. In certain embodiments according to the present invention the hydrogenation processes may be operated at moderate pressures to achieve acceptable rates of hydrogenation. Other embodiments of the invention include catalysts comprising a Group VIII metal deposited on a catalyst support material selected from graphite and silicon carbide. Yet other embodiments of the invention include catalysts consisting essentially of a Group VIII metal deposited on a catalyst support material selected from graphite and silicon carbide.

In one embodiment the invention relates to processes for the preparation of dimethyl cyclohexanedicarboxylates by the catalytic hydrogenation of dimethyl benzenedicarboxylates comprising contacting a dimethyl benzenedicarboxylate with hydrogen in the presence of a catalyst comprising a Group VIII metal deposited on a catalyst support material selected from graphite and silicon carbide.

In one embodiment the invention relates to processes for the preparation of dimethyl cyclohexanedicarboxylates by the catalytic hydrogenation of dimethyl benzenedicarboxylates comprising contacting a dimethyl benzenedicarboxylate with hydrogen in the presence of a catalyst consisting essentially of a Group VIII metal deposited on a catalyst support material selected from graphite and silicon carbide.

In another embodiment the invention relates to a process wherein the process is carried out at a temperature of about 140 to 400° C. and a pressure (total) of about 8 to 690 bars absolute (bara) and the catalyst comprises about 0.1 to 10 weight percent of one or more Groups VIII metals selected from palladium, platinum, ruthenium, nickel and combinations thereof, wherein the weight percent is based on the total weight of the catalyst and the support.

In another embodiment the invention relates to a process wherein the process is carried out at a temperature of about 140 to 260° C. and a pressure (total) of about 50 to 170 bars absolute (bara) and the catalyst comprises about 0.5 to 5 weight percent palladium, wherein the weight percentages are based on the total weight of the catalyst and the support.

In another embodiment the invention relates to a process wherein the catalyst further comprises about 0.01 to 2 weight percent nickel, ruthenium or a mixture thereof.

In another embodiment the invention relates to a process wherein the dimethyl benzenedicarboxylate comprises dimethyl terephthalate and the dimethyl cyclohexanedicarboxylate comprises dimethyl 1,4-cyclohexanedicarboxylate at a temperature of about 140 to 240° C. and a pressure (total) of about 50 to 170 bars absolute (bara) and the catalyst comprises about 0.5 to 5 weight percent palladium, wherein the weight percentages are based on the total weight of the catalyst and the support. In another embodiment the invention relates to a process wherein the catalyst further comprises about 0.01 to 2 weight percent nickel, ruthenium or a mixture thereof, wherein the weight percentages are based on the total weight of the catalyst and the support.

In another embodiment the invention relates to a process wherein the process comprises operation in a continuous mode.

In another embodiment the invention relates to a process wherein the process comprises contacting the dimethyl terephthalate with the catalyst in at least one fixed bed of catalyst.

In another embodiment the invention relates to a process wherein 1,4-dimethyl cyclohexanedicarboxylate is recycled to the reactor.

In one embodiment the invention relates to a process wherein the liquid space hourly velocity of the dimethyl cyclohexanedicarboxylate ranges from about 0.1 to about 10.

In one embodiment the invention relates to a process wherein the liquid space hourly velocity of the dimethyl cyclohexanedicarboxylate ranges from about 0.5 to about 5.

In one embodiment the invention relates to a process wherein the liquid space hourly velocity of the total liquid flow of dimethyl cyclohexanedicarboxylate and solvent ranges from about 1 to about 40.

DETAILED DESCRIPTION

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used herein, the articles "a," "an," and "the" include their plural referents unless the context clearly dictates otherwise. For example, reference to a "catalyst," is intended to include the processing or making of a plurality of catalysts. References to a composition containing or including "an" ingredient or "a" support material is intended to include other ingredients or other support materials, respectively, in addition to the one named.

By "comprising" or "containing" or "including," it is meant that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

Certain embodiments of the processes of the present invention may be carried out at a temperature in the range of the melting point of the dimethyl benzenedicarboxylate reactant, e.g., 140° C. for dimethyl 1,4-benzenedicarboxylate (dimethyl terephthalate) up to about 400° C. In some embodiments, the processes preferably are carried out at a temperature in the range of about 140 to 260° C. In some embodiments of the present invention, the lower temperature may range from 140 or 150 or 160 or 170 or 180 or 190 or 200 or 210, or 220 or 230 or 240 or 250 or 260 or 270 or 270 or 290 or 300 or 310 or 320 or 330 or 340 or 350 or 360 or 370 or 380 or 390° C. In some embodiments of the present invention, the upper temperature may range from 150 or 160 or 170 or 180 or 190 or 200 or 210, or 220 or 230 or 240 or 250 or 260 or 270 or 270 or 290 or 300 or 310 or 320 or 330 or 340 or 350 or 360 or 370 or 380 or 390 or 400° C. Other embodiments according to the present invention my combine any lower temperature range with any upper temperature range.

Although the processes may be carried out at pressures (total) in the range of about 8 to 690 bars absolute (bara), the present invention permits the achievement of good hydrogenation rates without the use of high pressures. In some embodiments of the present invention, the pressures (total) ranges from about 10 to about 500, or from about 25 to about 250, or about 50 to 170 bara.

Although the 1,2-, 1,3- and 1,4-isomers of dimethyl cyclohexanedicarboxylate may be prepared by one embodiment of the processes of this invention by the hydrogenation of the corresponding dimethyl benzenedicarboxylate, the processes are particularly useful in the manufacture of the 1,3- and, especially, the 1,4-isomers.

The processes of the invention may be carried out in a batch, semi-continuous or continuous mode using conventional chemical processing techniques. In another embodiment of the present invention the process comprises a combination of two or more of batch, semi-continuous or continuous modes. In certain embodiments according to the present invention, the mode of operation is a continuous process wherein a melt of a dimethyl benzenedicarboxylate is through one or more fixed beds of catalyst in a "trickle bed" manner. In one embodiment of the invention the melt comprises dimethyl benzenedicarboxylate and DMCD. In one embodiment of the invention the melt comprises dimethyl benzenedicarboxylate. In some embodiments of the present invention, a portion of the dimethyl cyclohexanedicarboxylate product is recycled to the feed port of the reactor and serves as a solvent for the reactant.

In some embodiments of the present invention, one or more inert, non-aromatic compounds, which are liquid under the operating conditions employed, may be used as a solvent or solvent mixture. Examples of suitable solvents include, but not limited to, alcohols, such as CHDM, and other esters.

The process may be operated in either an adiabatic or isothermal process. In trickle bed operation, the liquid hourly space velocity (LHSV; unit volume reactant fed per hour per unit volume catalyst) of the dimethyl cyclohexanedicarboxylate reactant feed may be in the range of about 0.1 to 10 with a preferred range of 0.5 to 5. In some embodiments the lower limit of the LHSV of the dimethyl cyclohexanedicarboxylate feed may be 0.1 or 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0. In some embodiments the upper limit of the LHSV of the dimethyl cyclohexanedicarboxylate feed may be 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the LHSV of the dimethyl cyclohexanedicarboxylate feed may be a combination of any lower limit with any upper limit listed above.

The LHSV for the total liquid flow (dimethyl cyclohexanedicarboxylate reactant plus solvent) may be in the range of 1 to 40. In some embodiments the lower limit of the LHSV of the total liquid flow may be 1.0 or 2.0 or 3.0 or 4.0 or 5.0 or 6.0 or 7.0 or 8.0 or 9.0 or 10 or 15 or 20 or 25 or 30 or 35. In some embodiments the upper limit of the LHSV of the total liquid flow may be 2.0 or 3.0 or 4.0 or 5.0 or 6.0 or 7.0 or 8.0 or 9.0 or 10 or 15 or 20 or 25 or 30 or 35 or 40. The range of the LHSV of the total liquid flow may be a combination of any lower limit with any upper limit listed above.

Hydrogen is typically fed to the reactor in excess of the stoichiometric quantity and normally is purged from the system. The rate of hydrogen purge is dependent on the temperature and pressure at which the process is operated.

The catalysts of the present invention comprise a Group VIII metal deposited on a catalyst support material selected from graphite and silicon carbide. Examples of the Group VIII metals that may be present on the supported catalysts include, but are not limited to, palladium, platinum, ruthenium, nickel and combinations thereof. In one embodiment of the present invention the total amount of Group VIII metal present may be about 0.1 to 10 weight percent based on the total weight of the catalyst. The lower limit of the weight percent of the Group VIII metal may be 0.1 or 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0. The upper limit of the weight percent of the Group VIII metal may be 0.2 or 0.3 or 04 or 0.5 or 0.6 or 0.7 or 0.8 or 0.9 or 1.0 or 2.0 or 3.0 or 4.0 or 5.0 or 6.0 or 7.0 or 8.0 or 9.0 or 10.0. The range of the weight percent of the Group VIII metal may be any combination of any lower limit with any upper limit. In another embodiment of the present invention catalysts comprise about 0.5 to 5 weight percent palladium wherein the weight percentages are based on the total weight of the catalyst, e.g., the total weight of the support material plus the Group VIII metal. In another embodiment of the present invention the catalysts further comprise about 0.5 to 5 weight percent palladium, optionally in combination with about 0.01 to 2 weight percent nickel, ruthenium or a mixture thereof, wherein the weight percentages are based on the total weight of the catalyst, e.g., the total weight of the support material plus the metals.

The graphite and silicon carbide support materials may be in the form of extrudates, granules, and pellets for use in fixed-bed reactor processes and powder for slurry processes. The shape of the supports may be, but are not limit to, cylindrical, spheres, stars or any type of multiple-lobe shapes. Depending on the particular support material employed and/or the method used to prepare a catalyst, the Group VIII metal may be deposited primarily on the surface of the support or distributed substantially throughout the support.

The catalysts may be prepared by conventional techniques such as impregnation of one or more Group VIII metals or Group VIII metal compounds on or into a graphite or silicon carbide support material. The Group VIII metals may be provided as zero valence metals or as oxidized metals in the form of compounds such as salts of inorganic or organic acids and organometallic complexes. In one embodiment, the support materials may be impregnated with one or more Group VIII metals by immersing the support material in a solution of a Group VIII metal compound in a suitable solvent such as water or an organic solvent. The support material then is dried and the metal compound is reduced to a Group VIII metal.

In one embodiment, the catalyst comprises a Group VIII metal deposited on a catalyst support material selected from graphite and silicon carbide. In one embodiment the catalyst typically comprises about 0.1 to 1 weight percent, based on the total weight of the catalyst, of one or more Groups VIII metals selected from palladium, platinum, ruthenium, nickel and combinations thereof. In another embodiment, catalyst comprises about 0.5 to 5 weight percent palladium, optionally in combination with about 0.01 to 2 weight percent nickel, ruthenium or a mixture thereof, deposited on a catalyst support material selected from graphite and silicon carbide, wherein the weight percentages are based on the total weight of the catalyst.

EXAMPLES

The following examples set forth preferred methods in accordance with the invention. It is to be understood, however, that these examples are provided by way of illustration and nothing therein should be taken as a limitation upon the overall scope of the invention.

The processes and catalysts provided by the invention are further illustrated by the following examples. All percentages are by weight unless specified otherwise. The graphite and silicon carbide support materials used in the examples were 1.6 mm (1/16 inch) extrudates obtained from Engelhard Corporation. The graphite support had a BET surface area of 791 square meters per gram and an average pore diameter of 3.2 nm. The silicon carbide support had a BET surface area of 1 square meter per gram and an average pore diameter of 5.5 nm. BET surface area refers to specific surface area described in detail in Brunauer, S., Emmet, P. H., and Teller, E., J. Am. Chem. Soc., 60, 309-16 (1938). Percent conversion of dimethyl terephthalate (DMT) is defined as:

$$\frac{\text{Moles } DMT \text{ converted to products}}{\text{Moles } DMT \text{ fed}} \times 100$$

and the percent selectivity to dimethyl 1,4-cyclohexanedicarboxylate (DMCD) is defined as $$\frac{\text{Moles } DMT \text{ converted to } DMCD}{\text{Moles } DMT \text{ converted to all products}} \times 100.$$

Example 1

Graphite extrudates (64 g) were added to a 500 cc glass filtration flask. A solution of palladium(II) acetate (2.71 g) in methyl acetate (70 cc) was added drop-wise to the flask, which was slowly rotated, until the graphite was completely wet. The addition of the palladium acetate solution saturated the graphite support material, i.e., no free or excess solution was present. Then, the flask was evacuated at about 0.1 bar absolute (bara) and then vented. The evacuation procedure was repeated three times. The purpose of evacuation is to assist the penetration and impregnation of the palladium acetate solution into the pores of the catalyst support material by removing air trapped inside the pores. The evacuation procedure provides a more uniform distribution of the catalytic metal on and in the catalyst support. The impregnated graphite extrudates were dried in an oven maintained at 100° C. The dried extrudates were added to 150 cc 2.6% sodium formate solution in a glass beaker maintained at 75-78° C. for 40 minutes to reduce the palladium(II) salt to palladium metal. The extrudates were separated from the solution and then rinsed with distilled/deionized water 10 times at room temperature. Finally, the extrudates were dried in an air circulating oven at 60° C. over night to provide 64 g of a 2% palladium on graphite catalyst.

Example 2

A 2% Pd/graphite catalyst (25 g) prepared according to the procedure described in Example 1 was placed in to a 500 cc glass filtration flask. A solution of 0.24 g of nickel(II) formate dihydrate in 50 g of distilled and deionized water was added drop-wise to the flask which was slowly rotated to completely wet the Pd/graphite. Then, the flask was evacuated at 0.1 bara and vented four times. The impregnated graphite extrudates were dries in an oven maintained at 100° C.

The dried extrudates were heated in flowing 20% hydrogen/helium (500 standard cubic centimeters per minute—SCCM) at 220° C. for 4 hours to provide 25 g of a catalyst consisting of 0.3% nickel and 2% palladium on graphite.

Example 3

Graphite extrudates (25 g) were placed in a 500 cc glass filtration flask. A solution of 2.0 g of ruthenium(III) acetylacetonate in 50 g of methyl acetate was added drop-wise to the flask, which was slowly rotated, to completely wet the graphite. The flask was evacuated at 0.1 bara and then vented four times. The impregnated graphite extrudates were dried in an oven maintained at 100° C. The dried extrudates were heated in flowing 20% hydrogen/helium (500 SCCM) at 220° C. for 4 hours to provide 25 g of a catalyst consisting of 2% ruthenium metal on graphite.

Example 4

A 2% Pd/graphite catalyst (25 g) prepared according to the procedure described in Example 1 was placed in a 500 cc glass filtration flask. A solution of 0.3 g of ruthenium(III) acetylacetonate in methyl acetate (25 g) was added drop-wise to the flask, which was slowly rotated, to completely wet the graphite. The flask then was evacuated at 0.1 bara four times. Then the impregnated graphite extrudates were dried in an oven maintained at 100° C. The dried extrudates were heated in flowing 20% hydrogen/helium (500 SCCM) at 220° C. for 4 hours to provide 25 g of catalyst consisting of 0.15% ruthenium and 2% palladium on graphite.

Example 5

A catalyst consisting of 2% palladium metal on silicon carbide was prepared according to the procedure described in Example 1 from 50 g of silicon carbide extrudates and a solution of palladium(II) acetate (2.12 g) in methyl acetate (15 cc). A solution of 0.197 g ruthenium(III) acetylacetonate and 15 g of methyl acetate was added dropwise to 50 g of the 2% Pd/SiC in a 500 c glass filtration flask, which was slowly rotated, to completely wet the 2% Pd/SiC. The flask was evacuated at 0.1 bara and then vented four times. The impregnated silicon carbide was dried in an oven maintained at 100° C. The dried extrudates were heated in flowing 20% hydrogen/helium (500 SCCM) at 220° C. for 4 hours to provide 50 g of catalyst consisting of 0.1% ruthenium and 2% palladium on silicon carbide.

Example 6

A catalyst consisting of 1% palladium metal on silicon carbide was prepared according to the procedure described in Example 1 from 50 g of silicon carbide extrudates and a solution of palladium(II) acetate (1.06 g) in methyl acetate (15 cc). A solution of ruthenium(III) acetylacetonate (1.75 g) in methyl acetate (39 g) was added dropwise added to 50 g of the 1% Pd/SiC in a 500 c glass filtration flask, which was slowly rotated, until the 0.5% Pd/SiC extrudates were completely wet. The flask was evacuated at 0.1 bara and then vented four times. The impregnated 1% Pd/SiC extrudates then were dried in an oven maintained at 100° C. and then cooled to ambient temperature. The impregnation procedure was repeated twice to utilize the remaining ruthenium(III) acetylacetonate-in-methyl acetate solution. Finally, the resulting dried extrudates were heated in flowing 20% hydrogen/helium (500 SCCM) at 220° C. for 4 hours to provide 50 g of catalyst consisting of 0.8% ruthenium and 1% palladium on silicon carbide.

Example 7

The catalyst produced in Example 1 (5 g) in a stainless steel catalyst basket was loaded in a 300 cc stainless steel autoclave. Then 170 g of DMCD and 30 g of DMT were added to the autoclave. Then, the autoclave was agitated and purged with 10 psig nitrogen twice at ambient temperature and then purged with 0.7 bars guage (barg) (10 psig) hydrogen. Then, the autoclave was heated to 200° C. at a heating rate of 10° C./minute and pressurized to 137.5 barg (2000 psig) with hydrogen. After 2 hours, the autoclave was cooled to about 70° C. and purged with nitrogen. Finally, the solution was discharged from the autoclave and analyzed by gas chromatography. DMT conversion was 68% and selectivity to DMCD was 95%.

Example 8

The catalyst produced in Example 2 (5 g) in a stainless steel catalyst basket was loaded in a 300 cc stainless steel autoclave. Then 170 g of DMCD and 30 g of DMT were added to the autoclave. Then, the autoclave was agitated and purged with 0.7 barg (10 psig) nitrogen twice at ambient temperature and then purged with 0.7 barg (10 psig) hydrogen. Then, the autoclave was heated to 200° C. at a heating rate of 10° C./minute and pressurized to 137.5 barg (2000 psig) with hydrogen. After 3 hours, the autoclave was cooled to about 70° C. and purged with nitrogen. Finally, the solution was discharged from the autoclave and analyzed by gas chromatography. DMT conversion was 73% and selectivity to DMCD was 98%.

Example 9

The catalyst produced in Example 3 (5 g) in a stainless steel catalyst basket was loaded in a 300 cc stainless steel autoclave. Then 170 g of dimethyl DMCD and 30 g of DMT were added to the autoclave. Then, the autoclave was agitated and purged with 0.7 barg (10 psig) nitrogen twice at ambient temperature and then purged with 0.7 barg (10 psig) hydrogen. Then, the autoclave was heated to 180° C. at a heating rate of 10° C./minute and pressurized to 137.5 barg (2000 psig) with hydrogen. After 3 hours, the autoclave was cooled to about 70° C. and purged with nitrogen. Finally, the solution was discharged from the autoclave and analyzed by gas chromatography. DMT conversion was 99% and selectivity to DMCD was 97%.

Example 10

The catalyst produced in Example 4 (5 g) in a stainless steel catalyst basket was loaded in a 300 cc stainless steel autoclave. Then 170 g of DMCD and 30 g of DMT were added to the autoclave. Then, the autoclave was agitated and purged with 0.7 barg (10 psig) nitrogen twice at ambient temperature and then purged with 0.7 barg (10 psig) hydrogen. Then, the autoclave was heated to 180° C. at a heating rate of 10° C./minute and pressurized to 2000 psig with hydrogen. After 3 hours, the autoclave was cooled to about 70° C. and purged with nitrogen. Finally, the solution was discharged from the autoclave and analyzed with a gas chromatography. DMT conversion was 99% and selectivity to DMCD was 97%.

Example 11

The catalyst produced in Example 5 (10 g) in a stainless steel catalyst basket was loaded in a 300 cc stainless steel autoclave. Then 170 g of DMCD and 30 g of DMT were added to the autoclave. Then, the autoclave was agitated and purged with 0.7 barg (10 psig) nitrogen twice at ambient temperature and then purged with 0.7 barg (10 psig) hydrogen. Then, the autoclave was heated to 200° C. at a heating rate of 10° C./minute and pressurized to 137.5 barg (2000 psig) with hydrogen. After 3 hours, the autoclave was cooled to about 70° C. and purged with nitrogen. Finally, the solution was discharged from the autoclave and analyzed by gas chromatography. DMT conversion was 83% and selectivity to DMCD was 92%.

Example 12

The catalyst produced in Example 6 (10 g) in a stainless steel catalyst basket was loaded in a 300 cc stainless steel autoclave. Then 170 g of DMCD and 30 g of DMT were added to the autoclave. Then, the autoclave was agitated and purged with 0.7 barg (10 psig) nitrogen twice at ambient temperature and then purged with 0.7 barg (10 psig) hydrogen. Then, the autoclave was heated to 200° C. at a heating rate of 10° C./minute and pressurized to 2000 psig with hydrogen. After 3 hours, the autoclave was cooled to about 70° C. and purged with nitrogen. Finally, the solution was discharged from the autoclave and analyzed by gas chromatography. DMT conversion was 71% and selectivity to DMCD was 91%.

The invention has been described in detail with particular reference to preferred embodiments thereof, but it will be understood that variations and modifications can be effected within the spirit and scope of the invention.

I claim:

1. A process for the preparation of dimethyl cyclohexanedicarboxylates by the catalytic hydrogenation of dimethyl benzenedicarboxylates, the process comprising contacting a dimethyl benzenedicarboxylate with hydrogen in the presence of a catalyst comprising a Group VIII metal deposited on a catalyst support material selected from graphite and silicon carbide, wherein the process is carried out at a temperature of about 140 to 260° C. and a pressure (total) of about 50 to 170 bars absolute (bara) and the catalyst comprises about 0.5 to 5 weight percent palladium, wherein the weight percentages are based on the total weight of the catalyst and the support.

2. The process according to claim 1 wherein the catalyst further comprises about 0.01 to 2 weight percent nickel, ruthenium or a mixture thereof.

3. The process according to claim 1 wherein the dimethyl benzenedicarboxylate comprises dimethyl terephthalate and the dimethyl cyclohexanedicarboxylate comprises dimethyl 1,4-cyclohexanedicarboxylate at a temperature of about 140 to 260° C. and a pressure (total) of about 50 to 170 bars absolute (bara) and the catalyst comprises about 0.5 to 5 weight percent palladium, wherein the weight percentages are based on the total weight of the catalyst and the support.

4. The process according to claim 3 wherein the catalyst further comprises about 0.01 to 2 weight percent nickel, ruthenium or a mixture thereof.

5. The process according to claim 3 wherein the process comprises operation in a continuous mode.

6. The process according to claim 5 wherein the process comprises contacting the dimethyl terephthalate with the catalyst in at least one fixed bed of catalyst.

7. The process according to claim 6 wherein 1,4-cyclohexanedicarboxylate is recycled to the reactor.

8. The process according to claim 6 wherein the liquid space hourly velocity of the dimethyl cyclohexanedicarboxylate ranges from about 0.1 to about 10.

9. The process according to claim 6 wherein the liquid space hourly velocity of the dimethyl cyclohexanedicarboxylate ranges from about 0.5 to about 5.

10. The process according to claim 6 wherein the liquid space hourly velocity of the total liquid flow of dimethyl cyclohexanedicarboxylate and solvent ranges from about 1 to about 40.

11. A process for the preparation of dimethyl cyclohexanedicarboxylates by the catalytic hydrogenation of dimethyl benzenedicarboxylates, the process comprising contacting a dimethyl benzenedicarboxylate with hydrogen in the presence of a catalyst comprising a Group VIII metal deposited on a catalyst support material selected from graphite.

12. A process for the preparation of dimethyl cyclohexane-1,4-dicarboxylate by the catalytic hydrogenation of dimethyl benzene-1,4-dicarboxylate, the process comprising contacting a dimethyl benzene-1,4-dicarboxylate with hydrogen in the presence of a catalyst comprising a Group VIII metal deposited on a catalyst support material selected from silicon carbide,
wherein the silicon carbide has an average pore diameter less than about 10 nm.

13. A process for the preparation of dimethyl cyclohexanedicarboxylates by the catalytic hydrogenation of dimethyl benzenedicarboxylates, the process comprising contacting a dimethyl benzenedicarboxylate with hydrogen in the presence of a catalyst comprising a Group VIII metal deposited on a catalyst support material selected from graphite and silicon carbide,
wherein the average pore diameter is less than about 10 nm.

14. The process according to claim 11, wherein the process is carried out at a temperature of about 140 to 400° C. and a pressure (total) of about 8 to 690 bars absolute (bara) and the catalyst comprises about 0.1 to 10 weight percent of one or more Groups VIII metals selected from palladium, platinum, ruthenium, nickel and combinations thereof, wherein the weight percent is based on the total weight of the catalyst and the support.

15. The process according to claim 12 wherein the process is carried out at a temperature of about 140 to 400° C. and a pressure (total) of about 8 to 690 bars absolute (bara) and the catalyst comprises about 0.1 to 10 weight percent of one or more Groups VIII metals selected from palladium, platinum, ruthenium, nickel and combinations thereof, wherein the weight percent is based on the total weight of the catalyst and the support.

16. The process according to claim 13, wherein the process is carried out at a temperature of about 140 to 400° C. and a pressure (total) of about 8 to 690 bars absolute (bara) and the catalyst comprises about 0.1 to 10 weight percent of one or more Groups VIII metals selected from palladium, platinum, ruthenium, nickel and combinations thereof, wherein the weight percent is based on the total weight of the catalyst and the support.

* * * * *